United States Patent [19]

Johnson

[11] Patent Number: 4,644,263
[45] Date of Patent: Feb. 17, 1987

[54] METHOD AND APPARATUS FOR MEASURING WATER IN CRUDE OIL

[75] Inventor: Irvin D. Johnson, Englewood, Colo.

[73] Assignee: Marathon Oil Company, Findlay, Ohio

[21] Appl. No.: 681,178

[22] Filed: Dec. 13, 1984

[51] Int. Cl.$^4$ ............................................ G01N 27/07
[52] U.S. Cl. .................................. 324/65 P; 73/61.1 R
[58] Field of Search .................... 73/861.04, 61.1 R; 324/65 R, 437, 448, 449, 65 P

[56] References Cited

U.S. PATENT DOCUMENTS

| | | | |
|---|---|---|---|
| 2,752,586 | 6/1956 | Jordan | 340/235 |
| 2,807,956 | 10/1957 | Doble | 73/73 |
| 2,913,893 | 11/1959 | Mathews et al. | 68/18 |
| 3,192,473 | 6/1965 | Marsh | 324/61 |
| 3,488,996 | 1/1970 | Pfrehm | 63/61.1 |
| 3,515,988 | 6/1970 | Shawhan | 324/30 |
| 3,792,347 | 2/1974 | Hawley | 324/65 R |
| 3,892,127 | 4/1975 | Cirulis et al. | 73/61.1 |
| 3,899,688 | 8/1975 | Perieres | 250/576 |
| 3,906,198 | 9/1975 | November | 235/151.35 |
| 3,909,709 | 9/1975 | Maxon | 324/30 |
| 4,030,028 | 6/1977 | Allender | 324/65 |
| 4,036,053 | 7/1977 | Jenkins | 73/295 X |
| 4,048,854 | 9/1977 | Herzl | 73/194 |
| 4,059,937 | 11/1977 | Dowling | 73/61.1 |
| 4,082,997 | 4/1978 | Ohtsu et al. | 324/65 |
| 4,112,744 | 9/1978 | Tassano | 73/61.1 |
| 4,116,045 | 9/1978 | Potter | 73/61.1 |
| 4,225,778 | 9/1980 | Ghahramani | 73/61.1 |
| 4,236,406 | 12/1980 | Reed et al. | 73/61.1 |
| 4,251,809 | 2/1981 | Cheney | 340/603 |
| 4,266,188 | 5/1981 | Thompson | 324/65 |
| 4,340,938 | 7/1982 | Rosso | 364/510 |
| 4,390,842 | 6/1983 | Wygant et al. | 324/439 |
| 4,404,516 | 9/1983 | Johnson, Jr. | 324/65 R |

Primary Examiner—Herbert Goldstein
Attorney, Agent, or Firm—Jack L. Hummel; Rodney F. Brown

[57] ABSTRACT

A method and apparatus for measuring the amount of fluids in a two-fluid mixture flowing in a conduit wherein the fluids have different electrical conductivities. The apparatus includes a predetermined grid pattern of a first plurarlity of horizontal and a second plurality of vertical wires all under tension wherein the vertical wires are spaced a predetermined distance from the horizontal wires. When the lower conductivity fluid, such as water, occupies the predetermined space at the intersection of a vertical and horizontal wire, an electrical signal is generated. The electrical signals generated from each predetermined spacing having the lower conductivity fluid there between are counted and the percentage concentration of the lower conductivity fluid in the higher conductivity fluid is determined for each time interval.

20 Claims, 11 Drawing Figures

METHOD AND APPARATUS FOR MEASURING WATER IN CRUDE OIL

BACKGROUND OF THE INVENTION

1. Field of the Invention

The present invention relates to measuring the percentage of water in crude oil flow and, more particularly, relates to a method and apparatus for determining the instantaneous conductivity of crude oil flow at a given location in a conduit to determine the percentage of water contained therein.

2. Discussion of Art

"Water-cut" monitors frequently are attached to pipelines containing crude oil flow in order to determine the water content of the crude oil flow. In fact, most lease agreements require that this type of measurement be made. In addition, it is often desirable to determine the water content of the production actually flowing down in a bore hole.

One common form of a "water-cut" monitor is a capacitance-probe. The probe is actually inserted into the pipe to determine the dielectric constant of the crude oil as it flows through the pipe. Changes in a dielectric constant are related to the amount of water in the flow and, therefore, the output signal is representative of the amount of water contained in the flow. Although capacitance "water-cut" monitors provide accuracy and reliability, such devices are expensive.

Prior to the filing of this application, a search was conducted of issued patents relating to the field of the present invention. The patents uncovered are:

| Inventor | Reg. No. | Issued |
| --- | --- | --- |
| O. D. Jordan | 2,752,586 | June 26, 1956 |
| F. C. Doble | 2,807,956 | Oct. 1, 1957 |
| M. B. Mathews | 2,913,893 | Nov. 24, 1959 |
| G. A. Marsh | 3,192,473 | June 29, 1965 |
| R. H. Pfrehm | 3,488,996 | Jan. 13, 1970 |
| E. N. Shawhan | 3,515,988 | June 2, 1970 |
| Cirulis et al. | 3,892,127 | July 1, 1975 |
| Perieres | 3,899,688 | Aug. 12, 1975 |
| November | 3,906,198 | Sept. 16, 1975 |
| Maxon | 3,909,709 | Sept. 30, 1975 |
| Allender | 4,030,028 | June 14, 1977 |
| Herzl | 4,048,854 | Sept. 20, 1977 |
| Dowling et al. | 4,059,987 | Nov. 29, 1977 |
| Ohtsu et al. | 4,082,997 | Apr. 4, 1978 |
| Tassano | 4,112,744 | Sept. 12, 1978 |
| Potter | 4,116,045 | Sept. 26, 1978 |
| Ghahramani | 4,225,778 | Sept. 30, 1980 |
| Reed et al. | 4,236,406 | Dec. 2, 1980 |
| Cheney | 4,251,809 | Feb. 17, 1981 |
| Thompson | 4,266,188 | May 5, 1981 |
| Rosso | 4,340,938 | July 20, 1982 |

The 1959 patent to Mathews sets forth a conductivity measuring device for use in dry-cleaning apparatuses which, as shown in FIGS. 3 through 7, utilizes electrical probes 39 and 40 longitudinally disclosed in a circular passageway for measuring the presence of water in a dry-cleaning solvent flowing therein. The 1975 patent to Maxon relates to an electrode 82 disposed in a circular passageway, as shown in FIG. 1 of Maxon, for measuring the conductivity of water in a gasoline mixture such as in a gas or fuel tank. The 1981 patent issued to Thompson discloses three probes for measuring the conductivity of a liquid in which they immerse such as in a pipe. The first probe is immersed in pure water, the second probe is immersed in pure oil, and the third probe is immersed in the actual flow. The 1977 Allender patent relates to a method and apparatus for detecting conductive particles in an oil flow system. The apparatus is placed in an areas of static oil flow and any metal particles in the oil flow will settle out and change the resistance of the circuit.

The remaining patents are not as close to the teachings of the present invention as those discussed above and pertain to other approaches such as: capacitance techniques (Rosso, Ghahramani, Tassano, Shawhan), specific gravity (Pfrehm), velocity of sound (Cirulis and Reed), heat of vaporization (Cheney), surface detection (Bronson and Ohtsu), volumetric ratios (Herzl), and optical detector (Perieres).

As the present invention relates primarily to "conductivity" water-cut probes, only the above discussed Mathews, Maxon, Thompson, and Allender patents are pertinent to the teachings of the present invention. As observed in the Mathews patent, the distribution of water in the flow (in the Mathews situation organic solvent) is not generally uniform over time. Furthermore, as found in Mathews et al, it is important that the conductivity electrodes not restrict the flow of fluids. Finally, it is noted in Mathews that the conductivity system operate continuously to measure the electrical conductivity of the fluid flow. As recognized in the Maxon patent, it is important that the electrical conductivity device not cause possible ignition of the flowing fluids. In addition, as also set forth in Maxon, the continuous application of current to the electrical probes can result in electrolysis thereby possibly rendering the device inaccurate and requiring frequent recalibration. The advantages of using a multiplexer to sample at rates of one to two hundred sets of measurements per second are set forth in the Thompson patent wherein three separate probes are inserted into the flowing fluid.

The present invention seeks to incorporate the advantages set forth above but, at the same time, improving upon the specifically discussed approaches. In particular, the present invention provides a three dimensional measurement of the amount of water in the crude oil flow by providing a number of instantaneous conductivity measurements at a plurality of locations in a plane located at angles substantially vertical to the flow of the fluids. Mathews, Maxon, and Thompson provide essentially a single instantaneous conductivity measurement in such a plane. The present invention utilizes a plurality of nodes all located in a plane substantially vertical or vertical to the flow of the fluids.

SUMMARY OF THE INVENTION

The problem faced in measuring instantaneous conductivity is to provide a method and apparatus which determines the instantaneous conductivity in a true three dimensional configuration of the flow of crude oil and water in a conduit. The present invention accomplishes this by providing a plurality of points for determining instantaneous conductivity wherein all of the points are located substantially vertical to the flow of the fluids in the pipe and wherein the points can be specifically oriented in the flow based on the characteristics of the flow. The provision of a plurality of measuring points in a substantial vertical plane provides two dimensions whereas the actual flow of the fluid provides the third dimension.

The present invention, therefore, includes a grid containing a plurality of electrical nodes wherein each of the nodes are sampled, in time, to determine their present voltage so that the instantaneous conductivity of the flow at the node can be determined. The grid is located at angles substantially vertical to the flow of the fluid. The wires utilized to establish the electrical grid of the present invention are sufficiently small so as not to interfere with the flow of the fluids in the pipe.

DESCRIPTION OF THE PREFERRED EMBODIMENT

Figure 1:
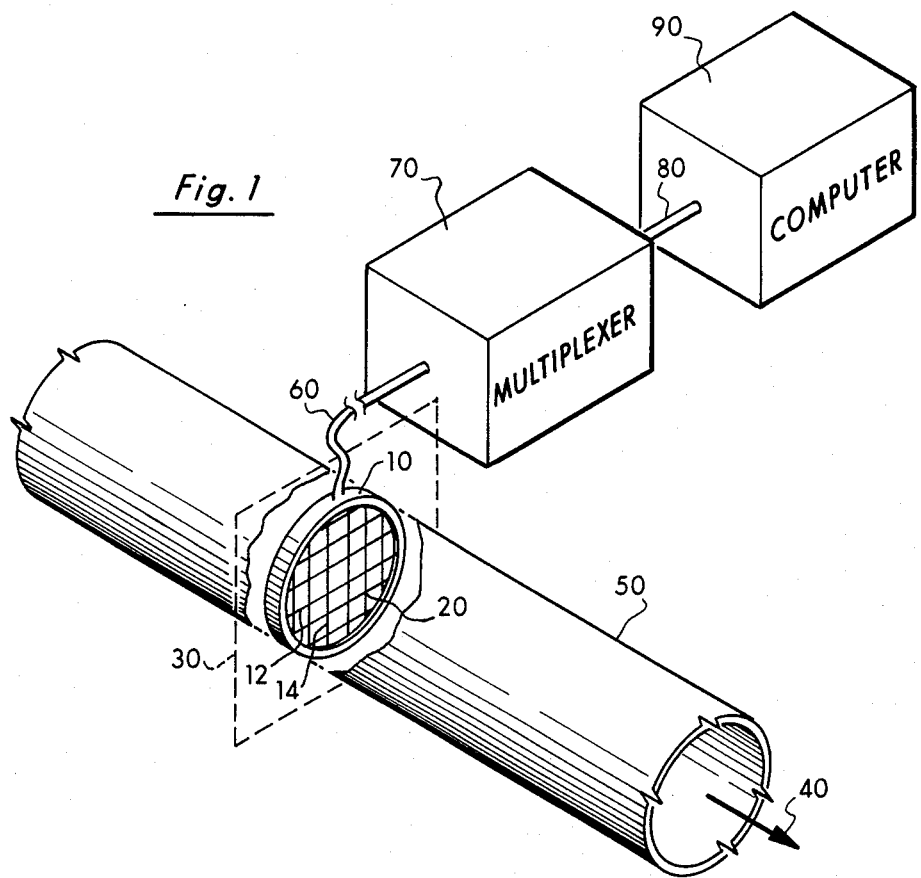
FIG. 1 illustrates a grid located in a conduit, the grid connected to a multiplexer and a computer.

In FIG. 1, the present invention is illustrated showing a grid 10 composed of horizontal wires 12 and vertical wires 14 having a plurality of nodes 20 all of which are located in a plane 30 substantially vertical to the flow 40 of fluids in a pipe or conduit 50. Electrical signals from the grid 10 are delivered over a cable 60 to a multiplexer 70 and thence over a cable 80 to a computer 90. As will become evident in FIG. 1, the plurality of nodes 20 in the grid provides a two dimensional analysis in plane 30 to the flow 40 of fluids in conduit or pipe 50. The actual flow 40, in time, of the fluid, of course, provides the third dimension for analysis.

Figure 2:
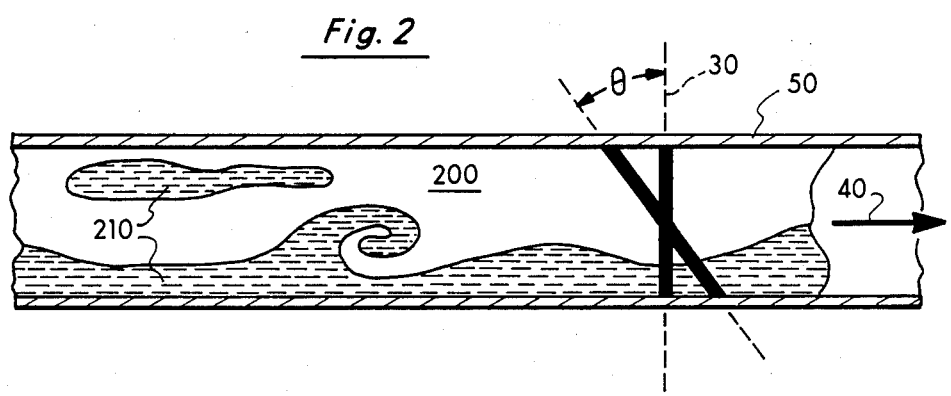
FIG. 2 illustrates water and oil flowing in a conduit.

In FIG. 2, the composition of water in crude oil flow includes the crude 200 intermixed with water 210. It can be observed in FIG. 2, that because of the intermixing of the two fluids 200 and 210, a three dimensional analysis over a period of time will provide an accurate measurement of the amount or percentage of water contained in the total flow 40 of the two fluids 200 and 210. The flow 40 can be comprised of any mixture of two fluids wherein one fluid has a greater electrical conductivity than the other.

In addition, and as shown in FIG. 2, the plane 30 can be oriented vertically as shown in FIG. 1 or substantially vertical at an angle, theta, from vertical as shown in FIG. 2. Such vertical or substantially vertical orientation provides two dimensions (across the surface of the conduit 50) whereas the time of the flow provides the third dimension. Slanting the plane 30 minimizes the surface tension between the nodes 20 and the fluids 200 and 210.

Figure 3:
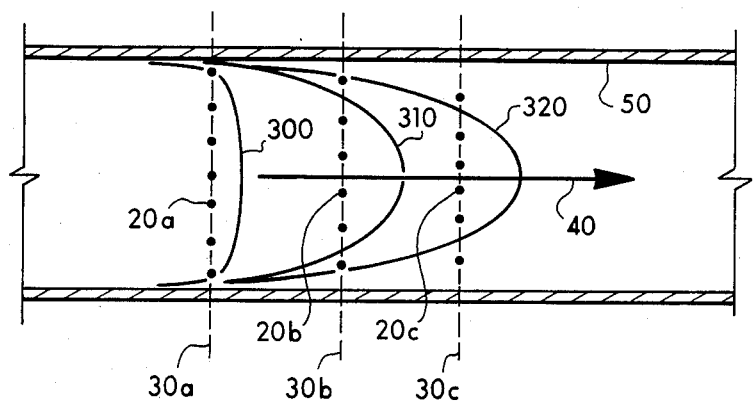
FIG. 3 illustrates flow curves of a fluid flowing in a conduit.

A further characteristic of the flow 40 is set forth in FIG. 3. In FIG. 3, flow curves 300, 310, and 320 are set forth for three different velocities of flow 40. Curve 300 shows turbulent flow which is a greater velocity and curve 300 shows laminar flow which is a lower velocity in the representation of FIG. 3. The curve 310 represents the transition between turbulent and laminar flow. The flow curves vary because of the drag occurring between the fluid and the inner surface of the conduit 50. It is well known, for example, that the flow 40 is greatest at the center of conduit 50 and that the flow has the slowest velocity near the inner surfaces of conduit 50. Hence, for lower rates of velocity for flow 40, a greater velocity distribution exists in flow curve 320 than in flow curve 300 and the nodes 20a, 20b, and 20c, located in plane 30a, 30b, and 30c respectively can be tailored in their spacing to more closely correspond to the flow pattern. Hence, for flows 40 of lower velocities as represented by curve 320, the nodes 20c can be more closely spaced around the center of the conduit 50 whereas the nodes 20a for flow curve 300 can be more uniformly spaced across the entire surface of conduit 50. The appropriate spacing for the nodes 20 are dependent upn the actual velocity of the production flow 40.

Figure 4:
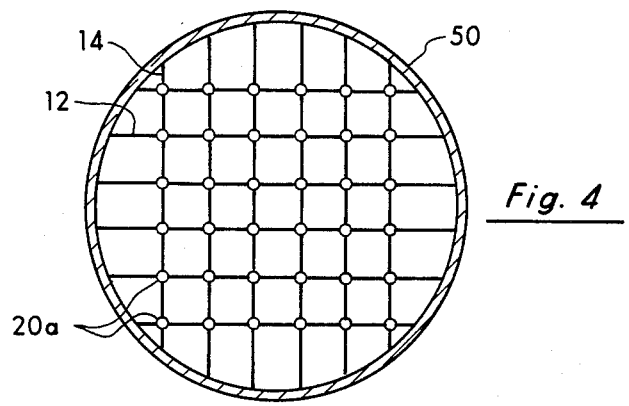
FIG. 4 illustrates arrangements of nodes in a conduit.
Figure 5:
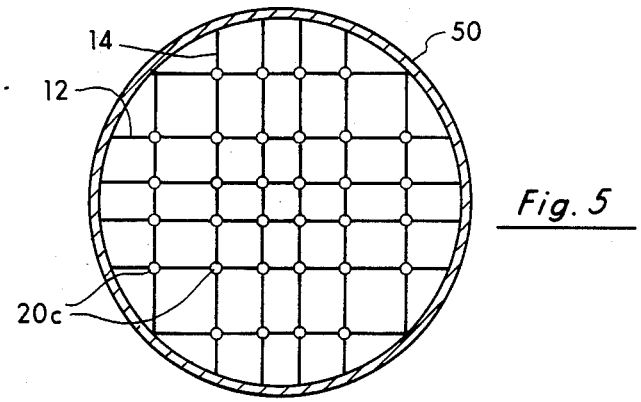
FIG. 5 illustrates a different arrangement of nodes in a conduit.

The arrangement of the nodes for planes 30a and 30c are shown in FIGS. 4 and 5 respectively and it can be readily observed in FIG. 5 that the nodes 20c are more heavily concentrated towards the center of the conduit 50 than they are in FIG. 4 which is representative of a lower velocity flow.

Figure 6:
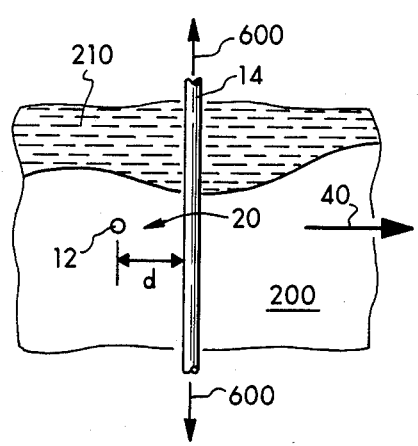
FIG. 6 illustrates crude oil and water in relation to vertical and horizontal wires in a grid.

The details of an individual node 20 are set forth in FIG. 6 wherein a vertical wire 14 is spaced from a horizontal wire 12 by a predetermined distance, d. In FIG. 6, crude oil 200 is shown to occupy the space of sphere of influence between the horizontal wire 12 and the vertical wire 14. When crude oil 200 occupies this space (i.e., node 20) an open circuit, or break in the electrical path, exists between electrical paths 12 and 14. Clearly, if water 210 is found in node 20, then a closed circuit or short exists between wires 12 and 14 and the wires become electrically connected. Hence the electrical node 20 of the present invention enables a positive determination (i.e., either an open or a short) dependent upon the presence of crude 200 or water 210, respectively.

It is also clear from inspection of FIG. 6, that the wires 12 and 14 must each be under a tension 600 so that wire 12, for example, is not pushed in the direction of wire 14 so as to establish physical contact therewith under the forces exerted by the flow 40. Hence, in the preferred embodiment, the wires 12 and 14 are of small diameter on the order of 0.025 inches (number 22 wire) with a spacing d, between the wires on the order of 0.05 inches. Furthermore, a tension of approximately ten pounds is typically provided but any tension which is great enough to prevent physical contact between wires 12 and 14 would be suitable. It is clear, that wires of such small diameter will not impede the flow 40 in any fashion.

Figure 7:
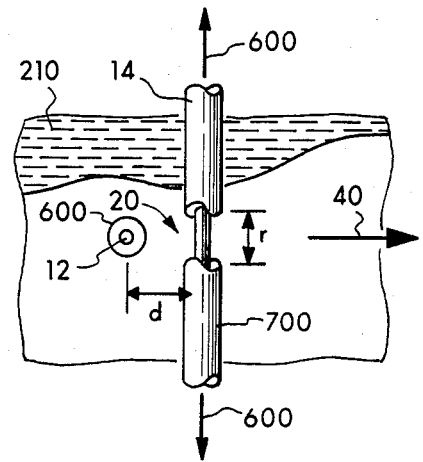
FIG. 7 illustrates crude oil and water flowing past a horizontal and vertical wire in a grid wherein the wires are insulated.

In FIG. 7, a variation of the embodiment of FIG. 6 is set forth wherein the wires 12 and 14 may have insulation around each of the wires except at a defined region, r, at the area of the node. This serves to reduce the sphere of influence or volume of the sampling point at node 20 so as to prevet overlap with adjacent nodes.

Figure 8:
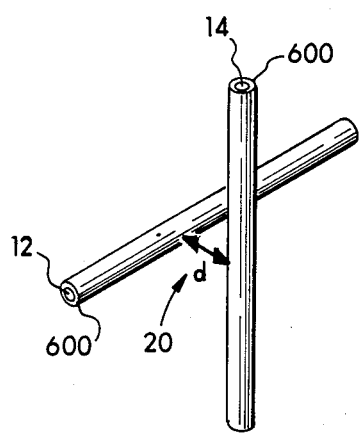
FIG. 8 illustrates illustration around the vertical and horizontal wires in a grid.

A third variation, shown in FIG. 8, would involve the wires 12 and 14 fully insulated even in the area of the node 20. The advantage of this configuration over the configuration shown in FIGS. 6 and 7 would be a physical embodiment that minimizes the corrosive effect of the fluid environment on the wires 12 and 14. In other words, the presence of insulation 600 would prevent corrosive build-up. However, the embodiment shown in FIG. 8 does not provide a pure conductivity measurement as that shown in FIGS. 6 and 7 but rather would be properly categorized as a capacitive measurement wherein the presence or absence of conductive fluids such as water 210 dramatically affects the dielectric constant between wires 12 and 14.

Figure 9:
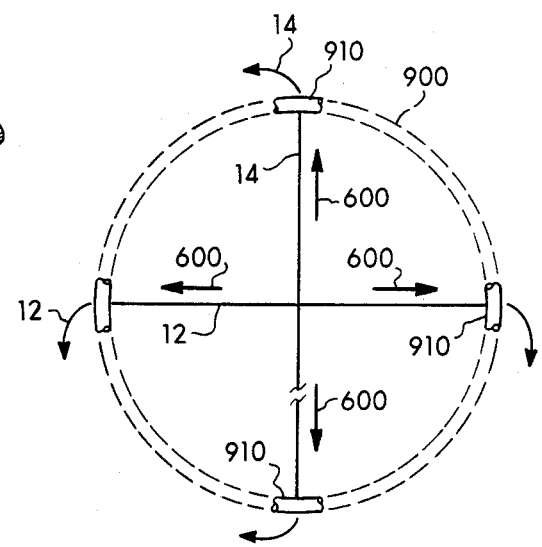
FIG. 9 illustrates a rim designed to hold wires in the grid in place.

In FIG. 9, a rim 900 which is designed to engage the conduit 50 at the desired location in a fluid type relationship is provided wherein various connectors 910 are utilized to hold each wire 14 (or 12) in tension 600 across the rim 900 so that output leads 14 are provided which carries the signals to and from the nodes 20.

Figure 10:
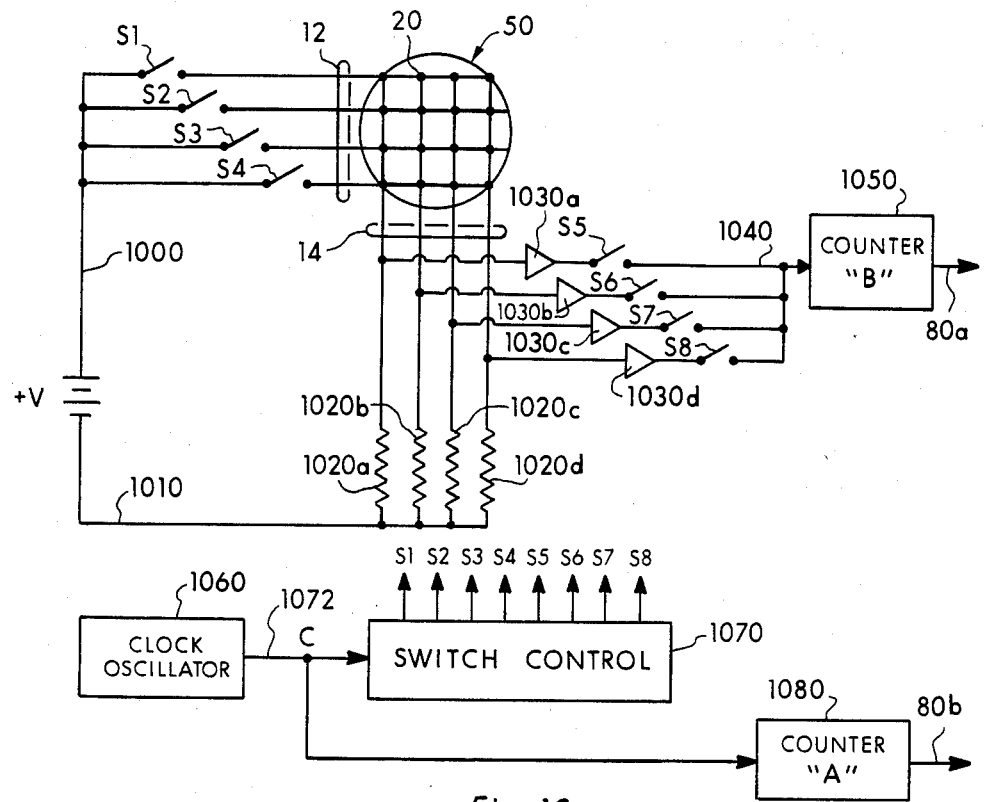
FIG. 10 illustrates the electrical circuitry of the multiplexer.

In FIG. 10, are set forth the circuit details of the multiplexer 70 of the present invention. In this embodiment, four horizontal wires 12 and four vertical wires 14 create a total of sixteen nodes 20. The four vertical wires access four solid state switches, S1 through S4, which are commonly tied together on line 1000 to access a voltage source such as positive voltage +V. It is to be expressly understood that any suitable voltage source such as a negative source or even an AC source could be used. The positive voltage source is also interconnected over line 1010 to a bank of resistors 1020a through 1020d. Each of these resistors are interconnected to individual vertical lines 14 aind to a bank of operational amplifiers 1030a through 1030d which in turn are connected to a bank of solid state switches S5 through S8. The output of solid state switches S5 through S8 are commonly tied to line 1040 to access a counter 1050. The output of counter 1050 is delivered over line 80a to the computer 90 as shown in FIG. 1. A clock oscillator 1060 is also provided which accesses a multiplex switch control 1070 over line 1072 and which further accesses over line 1072 a second counter 1080. The output of counter 1080 is delivered over 80b to computer 90. The output of the switch control 1070 is delivered to each individual solid state switch S1 through S8.

The components set forth in FIG. 10 are available from a variety of sources such as, for example:
 1. Solid state switches S1-S8—AH5011 (National Semiconductor)
 2. Clock oscillator 1060—CD4011 (RCA Corp.)
 3. Operational amplifier 1030—741 (National Semiconductor
 4. Multiplex switch control 1070—CD4012 (RCA Corp.)
 5. Counters 1050 and 1080—CD4516 (RCA Corp.)
In addition, isolation to the inputs of the operational amplifiers 1030 as well as impedance matching may be utilized. It is to be expressly uderstood that a number of circuit configurations could be utilized under the teachings of the present invention, the operation of which is now set forth.

Figure 11:
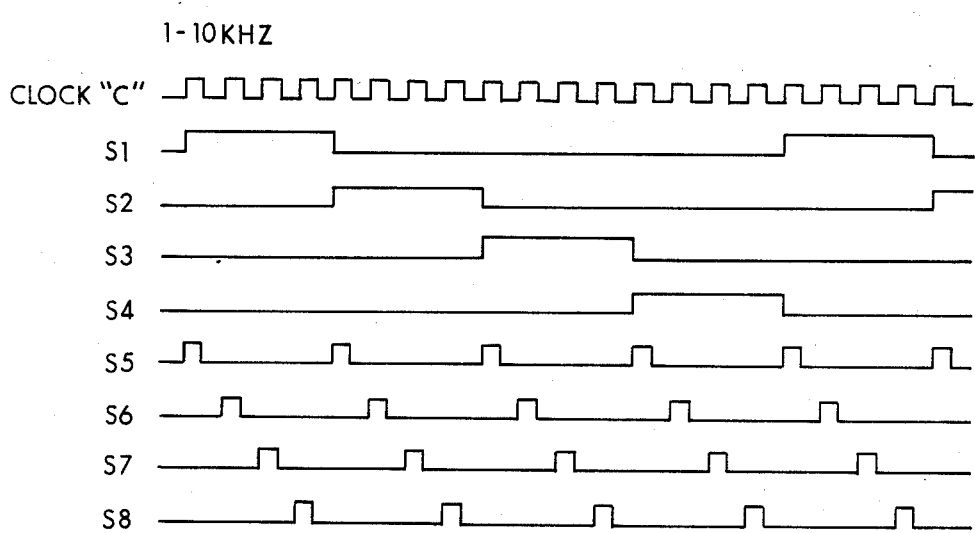
FIG. 11 illustrates the timing chart regarding the multiplexer operation.

The operation of the multiplexer 70 as shown in FIG. 10 is best explained by reference to the timing chart of FIG. 11. The output of the clock oscillator 1060 is preferably from one to ten kilohertz in frequency. Switches S1 through S4 are activated, in successive orders, after the completion of each four periods of the clock cycle. Switches S5 through S8 are activated with each period of the clock cycle in successive order. Hence, when switch S1 is closed for four clock cycles, each clock cycle in that four clock cycle interval successively activates switches S5 through S8 as shown in FIG. 11. For example, when switch S1 is closed and switch S5 is closed, an individual discrete node is activated. If water is present at the node, a short exists at the node and a circuit is completed from positive voltage through closed switch S1 through resistor 1020a and the operational amplifier detects the full voltage +V across the resistor 1020a. That positive voltage signal delivered through the operational amplifier 1030a over line 1040 and into the counter 1050 where it is counted. However, if crude oil is at the selected node, an open circuit exists and a very low voltage or ground signal is detected across resistor 1020a by operational amplifier 1030a and the counter 1050 does not count that pulse.

In this fashion, each of the nodes 20 in the grid pattern shown in FIG. 10, is selectively interrogated according to the timing chart of FIG. 11 and all nodes that have water are counted by counter 1050 as a "one" or "high" signal. For example, if four nodes have water, a count of four will exist in counter 1050 whereas a count of sixteen clock cycles will exist in counter A. The ratio of the count in counter B to the value in counter A provides the percentage amount of water, in a two dimensional analysis, in the conduit 50. Hence, for this example, a concentration of twenty-five percent water is detected.

In Table I, the hypothetical results for ten sixteen cycle clock periods are set forth. Each time slice represents a two dimensional analysis of the fluids in conduit 50. However, the three dimensional analysis performed in computer 90 results with a summation of the ratios over a a period of time and, for the example set forth in Table I, the resultant ratio is 28% water which is representative of the actual amount of water in the flow.

TABLE I

| Time | "B" Count | Ratio |
| --- | --- | --- |
| 1 | 4 | 0.250 |
| 2 | 4 | 0.250 |
| 3 | 6 | 0.375 |
| 4 | 8 | 0.500 |
| 5 | 8 | 0.500 |
| 6 | 4 | 0.250 |
| 7 | 5 | 0.313 |
| 8 | 4 | 0.250 |
| 9 | 2 | 0.125 |
| 10 | 0 | 0.000 |

It can be observed, that by increasing the number of nodes 20, by increasing the frequency of the clock 1060, and/or by tailoring the orientation of the nodes to the flow, greater accuracy can be obtained. However, this may increase the amount of data that must be processed by the computer 90 and, therefore, a practical trade-off can be made between the amount of data to be stored and the degree of accuracy required. In order to provide a three dimensional analysis of the water content of the flow 40, at least two nodes 20 and two time samplings are required.

It is obvious, therefore, that changes and modifications could be made to the system and method of the present invention, as defined in the following claims, without departing from the spirit and scope of the invention. For example, the use of the terms "horizontal" and "vertical" to describe the wires of the grid of the presentation invention are terms of relationship only and the wires could be oriented at any suitable angle in the conduit and, indeed, the wires need not be perpendicular to each other.

I claim:

1. A method for measuring the percentage of fluids in a two-fluid mixture flowing in a conduit, wherein the two fluids have different electrical conductivities, said method comprising the steps of:

in a given predetermined time period, measuring the instantaneous conductivity of the fluid located between a pair of electrical points spaced a predetermined distance apart at each one of a plurality of nodes arranged in a grid, each of said nodes being comprised of said pair of electrical points, said grid being located in a plane oriented at a substantially vertical angle to the flow of said two-fluid mixture in said conduit, repeating the aforesaid step of each successive predetermined period of time, and statistically determining the percentage of each fluid in said mixture over said successive periods of time.

2. A method for measuring the percentage of fluids in a two-fluid mixture flowing in a conduit, wherein the two fluids have different electrical conductivities, said method comprising the steps of:

in a given predetermined time period:
(a) successively sensing the instantaneous conductivity of the fluid located between a pair of electrical points spaced a predetermined distance apart at each one of a plurality of nodes arranged in a grid, each of said nodes being comprised of said pair of electrical points, said nodes being located in a plane oriented in a substantially vertical angle to the flow of said two-fluid mixture in said conduit,
(b) delivering a conductivity signal into a first counter for each sensed node having the lower conductivity fluid at said node,
(c) counting all delivered conductivity signals with said first counter,
(d) counting all sensed nodes with a second counter, and
(e) determining the ratio of the count in said first counter to the count in said second counter, said ratio being representative of the percentage of lower conductivity fluid to said total fluid flow, repeating the aforesaid step for each successive predetermined period of time, and averaging the ratios of the lower conductivity fluid to the higher conductivity fluid in said mixture flowing in said conduit over all predetermined periods of time.

3. A method for measuring the percentage of water in an oil/water mixture flowing in a conduit, said method comprising the steps of:

in a given predetermined time period:
(a) successively sensing the instantaneous conductivity of the fluid located between a pair of electrical points spaced a predetermined distance apart at each one of a plurality of nodes arranged in a predetermined grid pattern in the conduit, each of said nodes being comprised of said pair of electrical points,
(b) delivering a conductivity signal into a first counter for each sensed node having water at said node,
(c) counting all delivered conductivity signals with said first counter,
(d) counting all sensed nodes with a second counter, and
(e) determining the ratio of the count in said first counter to the count in said second counter, said ratio being representative of the percentage of water to said total fluid flow, repeating the aforesaid step for each successive predetermined period of time, and averaging the ratios of the lower conductivity fluid to the higher conductivity fluid in said mixture flowing in said conduit over all predetermined periods of time.

4. An apparatus for measuring the percentage of fluids in a two-fluid mixture (200, 210) flowing in a conduit (50), wherein the two fluids have different electrical conductivities, said apparatus comprising:

a sensor (10) connected to said conduit (50) having a plurality of vertical wires (14) and a plurality of horizontal wires (12) under tension (600), said horizontal wires (12) being spaced a predetermined distance (d) from said vertical wire (14) to form a predetermined grid of pattern of nodes (20) at the intersection of said vertical and horizontal wires, said sensor being located in a plane (30) substantially vertical (theta) to the flow of fluids in said conduit (50), a voltage source, a plurality of resistive loads (1020), means (S1-S4, 1070) connected to said voltage source and to said resistive loads (1020) for selectively applying said voltage to each of said nodes (20) and through one of said resistive loads (1020) in a predetermined period of time, means (S5-S8, 1070) connected to said nodes for generating a conductivity signal for each node (20) having the lower conductivity fluid (210) located in its predetermined spacing (d), means (1050) receptive of said conductivity signals from said generating means for counting said conductivity signals for each predetermined period of time, and means (1080) connected with said applying means for counting the number of nodes (20) having the voltage selectively applied thereto in each predetermined period of time, the ratio of the count of said voltage signals to the count of said nodes for each predetermined period of time when averaged over all predetermined periods of time being representative of the percentages of said low conductivity fluid (210) and said high conductivity fluid (200).

5. An apparatus for measuring the percentage of fluids in a two-fluid mixture (200, 210) flowing in a conduit (50), wherein the two fluids have different electrical conductivities, said apparatus comprising:

means (10) connected to said conduit (50) having a first plurality of wires (14) under tension (600) and a second plurality of wires (12) under tension (600), said second plurality of wires (12) being perpendicular to and being spaced a predetermined distance (d) from said first plurality wires (14) to form a predetermined grid pattern of nodes (20) at the intersections of said first and second plurality of wires, means (S1-S4, 1070), during a predetermined time period, for applying a voltage to each node (20), generating a signal for each node (20), means (S5-S8, 1070) connected to said nodes for generating a signal for each node (20) having the lower conductivity fluid (210) located in its predetermined spacing (d), means (1050) receptive of said signals from said generating means for counting said signals for each predetermined period of time, and means (1080) connected to said counting means for determining the number of counted nodes (20) generating a signal in each predetermined period of time, the ratio of the count of said generated signals to the number of said nodes for each predetermined period of time when averaged over all predetermined periods of time being representative of the percentages of said low conductivity fluid (210) and said high conductivity fluid (200) in said mixture flowing in said conduit.

6. The apparatus of claim 5 wherein each of said first and second plurality of wires further comprise insulation around said wires the entire length of said wires.

7. The apparatus of claim 5 wherein each of said first and second plurality of wires further comprise insulation around said wires except in the area of each node, said insulation extending the entire length of said wires.

8. An apparatus for measuring the percentages of fluids in a two-fluid mixture (200, 210) flowing in a conduit (50), wherein the two fluids have different electrical conductivities, said apparatus comprising:
  means (10) connected to said conduit (50) having a first plurality of wires (14) under tension (600) and a second plurality of wires (12) under tension (600), said second plurality of wires (12) being perpendicular to and being spaced a predetermined distance (d) from said first plurality wires (14) to form a predetermined grid pattern of nodes (20) at the intersections of said first and second plurality of wires,
  means (S1-S4, 1070) for applying a voltage to each node (20),
  means (S5-S8, 1070) connected to said nodes for generating a signal for each node (20) having the lower conductivity fluid (210) located in its predetermined spacing (d)
  means (1050) receptive of said signals from said generating means for counting said signals, and
  means (1080) connected to said counting means for determining the number of counted nodes (20) generating a signal, the ratio of the count of said generated signals to the number of said nodes being representative of the percentages of said low conductivity fluid (210) and said high conductivity flow (200) in said mixture flowing in said conduit.

9. The apparatus of claim 8 wherein each of said first and second plurality of wires comprise insulation around said wires the entire length of said wires.

10. The apparatus of claim 8 wherein each of said first and second plurality of wires further comprise insulation around said wires except in the area of each node, said insulation extending the entire length of said wires.

11. An apparatus for measuring the percentage of fluids in a two-fluid mixture (200, 210) flowing in a conduit (50), wherein the two fluids have different electrical conductivities, said apparatus comprising:
  means (10) connected to said conduit (50) for providing a predetermined grid pattern of nodes (20) in said conduit, each of said nodes being comprised of a pair of electrical points located a predetermined spacing apart,
  a power source,
  means (S1-S4, 1070) connected to said power source for selectively applying said power to each of said nodes (20) of said providing means in a predetermined period of time,
  means (S5-S8, 1070) connected to said nodes for generating a signal for each node (20) having the lower conductivity fluid (210) located in its predetermined spacing, and
  means (1080) connected with said generating means for counting the number of nodes (20) generating a signal in each predetermined period of time, the ratio of the count of said generated signals to the count of said nodes for each predetermined period of time when averaged over all predetermined periods of time being representative of the percentages of said low conductivity fluid (210) and said high conductivity fluid (200) in said mixture flowing in said conduit.

12. The apparatus of claim 11 wherein said predetermined grid pattern has more nodes oriented towards the center of said conduit (50) when the flow of said two-fluid mixture is laminar in nature.

13. The apparatus of claim 11 wherein said predetermined grid pattern has said nodes oriented with substantially uniform spacings across said conduit (50) when the flow of said two-fluid mixture is turbulent in nature.

14. The apparatus of claim 11 wherein said providing means is oriented substantially vertical in said conduit (50).

15. The apparatus of claim 11 wherein said providing means is oriented vertical to said conduit (50).

16. An apparatus for measuring the percentage of water in an oil/water mixture (200, 210) flowing in a conduit (50), said apparatus comprising:
  a sensor (10) connected to said conduit (50) having a plurality of vertical wires (14) and a plurality of horizontal wires (12), said horizontal wires (12) being spaced a predetermined distance (d) from said vertical wires (14) to form a grid of nodes (20) at the intersections of said vertical and horizontal wires, said sensor being located in a plane (30) substantially vertical angle (theta) to the flow of fluids in said conduit (50),
  a voltage source,
  a plurality of resistive loads (1020),
  means (S1-S8, 1070) connected to said voltage source for selectively applying said voltage to each of said nodes (20) and through one of said resistive loads (1020) in predetermined periods of time,
  means (S5-S8, 1070) connected to said nodes for generating a conductivity signal for each node (20) having water (210) located in its predetermined spacing (d), and
  means (1050) receptive of said conductivity signals from said generating means for counting said conductivity signals for each predetermined period of time, said count being representative of the percentage of water in said mixture.

17. An apparatus for measuring the percentage of water in an oil/water mixture (200, 210) flowing in a conduit (50), said apparatus comprising:
  a sensor (10) connected to said conduit (50) having a plurality of vertical wires (14) and a plurality of horizontal wires (12), said horizontal wires (12) being spaced a predetermined distance (d) from said vertical wires (14) to form a grid of nodes (20) at the intersections of said vertical and horizontal wires, said sensor being located in a plane (30) substantially vertical angle (theta) to the flow of fluids in said conduit (50),
  a voltage source,
  a plurality of resistive loads (1020),
  means (S1-S8, 1070) connected to said voltage source for selectively applying said voltage to each of said nodes (20) and througuh one of said resistive loads (1020) in predetermied periods of time, means (S5-S8, 1070) connected to said nodes for generating a signal for each node (20) having water (210) located in its predetermined spacing (d), and means (1050) receptive of said signals from said generating means for counting said signals for each predetermined period of time, said count being representative of the percentage of water in said mixture.

18. The apparatus of claim 17 wherein said horizontal and vertical wires further comprise insulation around said wires the entire length of said wires.

19. The apparatus of claim 17 wherein said horizontal and vertical wires further comprise insulation around said wires except in the area of each node, said insulation extending the entire length of said wires.

20. The apparatus of claim 11 wherein said pair of electrical points in each said node are formed from a first plurality of wires (14) oriented substantially perpendicularly to a second plurality of wires (12).

* * * * *